United States Patent [19]

Hayano et al.

[11] Patent Number: 5,742,290

[45] Date of Patent: Apr. 21, 1998

[54] MOLECULAR ORBITAL MODELING SYSTEM WITH AN IMPROVED FUNCTION PROCESSOR

[75] Inventors: Tomoaki Hayano; Azuma Matsuura, both of Kawasaki, Japan

[73] Assignee: Fujitsu Limited, Kawasaki, Japan

[21] Appl. No.: 714,286

[22] Filed: Sep. 18, 1996

Related U.S. Application Data

[63] Continuation of Ser. No. 115,098, Sep. 2, 1993, abandoned.

[30] Foreign Application Priority Data

Sep. 3, 1992 [JP] Japan .................................. 4-236145

[51] Int. Cl.$^6$ ....................................................... G09B 23/06
[52] U.S. Cl. ........................... 345/419; 345/501; 364/578; 434/283
[58] Field of Search ............................... 395/118.19, 140, 395/919–20, 501–2, 515, 118–19, 440, 511–15; 364/73.13, 413.15, 468.04, 408.09, 468.1; 434/277–81, 283, 277.81

[56] References Cited

U.S. PATENT DOCUMENTS

| | | | |
|---|---|---|---|
| 4,061,904 | 12/1977 | Hannauer et al. | 235/150.53 |
| 5,025,388 | 6/1991 | Cramer, III et al. | 364/496 |
| 5,075,767 | 12/1991 | Takaragi | 358/75 |
| 5,228,119 | 7/1993 | Mihalisin et al. | 395/118 |
| 5,268,854 | 12/1993 | Ikumi | 364/736 |
| 5,278,781 | 1/1994 | Aono et al. | 364/736 |
| 5,282,251 | 1/1994 | Yamada | 364/554 |
| 5,307,287 | 4/1994 | Cromer, III et al. | 364/496 |
| 5,325,198 | 6/1994 | Hartley et al. | 348/180 |
| 5,396,416 | 3/1995 | Berkowitz et al. | 364/165 |
| 5,408,596 | 4/1995 | Nonaka et al. | 395/140 |

OTHER PUBLICATIONS

"Kureha Chemical Industry Markets Molecular Design Support 3 System Developed Jointly with Fujitsu", *Fujitsu Weekly*, published by Digitized Information, Inc., Oct. 16, 1992, vol. 8, No. 4.

Fletterick, et al, "Computer Graphics and Molecular Modeling", appearing in *Current Communications in Molecular Biology*, Cold Spring Habor Laboratory, pp. 1–33, 1986.

Toma, "Protein Three–dimensional Structure Generation with an Emperical Hydrophic Penalty Function", Journal of Molecular Graphics, vol. 11, pp. 222–232, Dec. 1993.

Hinds, et al, "A Lattice Model for Protein Structure Prediction at Low Resolution", *Proc. Natl. Acad. Sci.*, vol. 89, pp. 2536–2540, Apr. 1992.

*Computer Graphics*, Foley et al; Addison Wesley 2ed 1990.

CRC *Standard Mathematical Tables*, CRC Publication, 25 ed 1978.

*Primary Examiner*—Joseph H. Feild
*Assistant Examiner*—Rudolph J. Buchel
*Attorney, Agent, or Firm*—Stass & Halsey

[57] ABSTRACT

A function processing system processes functions to make a three-dimensional display on a screen of a display means by connecting a plurality of lattice points of a space coordinate in a three-dimensional space region. The function processing system includes a computing system for computing a function value at each of the lattice points by a multivariable function having the space coordinate as an independent variable, where the computing system replaces the multivariable function by a product of a predetermined number of single variable functions and computing each of the single variable functions in advance so that the multivariable function is computed based on function values of each of the single variable functions, and a storage unit for storing the function values of the single variable functions which are computed in advance by the computing system. The computing system reads the stored function values of the single variable functions from the storage unit when computing the multivariable function.

23 Claims, 11 Drawing Sheets

MOLECULAR ORBITAL MODELING SYSTEM WITH AN IMPROVED FUNCTION PROCESSOR

This application is a continuation of application Ser. No. 08/115,098, filed Sep. 2, 1993, now abandoned.

BACKGROUND OF THE INVENTION

The present invention generally relates to function processing systems, and more particularly to a function processing system which computes variable function values of three-dimensional space lattice points in a computer system.

Recently, due to the high processing speed of computers, the use of processing systems for supporting design of materials by predicting characteristics of various material molecules using theoretical chemical calculations is gradually becoming popular. Such systems are often referred to as molecular design support systems. The molecular design support system is provided with a display unit such as a graphic display unit, and visualizes the results of the theoretical chemical calculations three-dimensionally so as to facilitate the analysis of the calculated results. In order to visualize the calculated results on the display unit at a high speed, there are demands to make the calculations in the molecular design support system at a high speed prior to the display so as to obtain the calculated values of the functions at the lattice points within the space region.

Conventionally, the molecular design support system is used for the theoretical chemical calculations when designing a material by predicting the characteristics of the material molecules. The calculated results are visualized three-dimensionally on the display unit so as to facilitate the analysis.

When visualizing on the display unit multivariable functions which are information related to electrons obtained by the theoretical chemical calculations, the function at each lattice point within the three-dimensional space region to be displayed is computed. In this case, in order to maintain the high-speed operability of the system, the number of lattice points within the three-dimensional space region is normally reduced so as to reduce the number of computations of the multivariable functions, so that the three-dimensional visualization of the multivariable functions can be realized at a high speed.

However, if the number of lattice points is reduced, the visualized image will lack precision. For this reason, an external input means is provided so that the number of lattice points can be increased if there is a demand to visualize a more precise image.

Next, a description will be given of the calculation of the function at each lattice point.

It will be assumed that a function to be calculated at each lattice point is a function having three-dimensional space coordinates x, y and z as its independent variables, and that is made up of a linear combination of N functions $\chi_i$ similarly having the three-dimensional space coordinates x, y and z as the independent variables. In addition, if it is assumed that this function $\chi_i$ can be described by a product of single variable functions each made up of the independent variables, the function $\psi(x, y, z)$ can be described by the following formula (1), where $f_i$, $g_i$ and $h_i$ are single variable functions respectively having x, y and z as the independent variable, and $c_i$ is a value which is derived from information which obtained in general by theoretical chemical calculations.

$$\psi(x,y,z) = \sum_{i=1}^{N} c_i \chi_i(x,y,z) \quad (1)$$

$$= \sum_{i=1}^{N} c_i f_i(x) g_i(y) h_i(z)$$

The space region of the three-dimensional lattices will be defined by $x_{min}$ to $x_{max}$, $y_{min}$ to $y_{max}$ and $z_{min}$ to $z_{max}$. In addition, the number of lattice points at each of the coordinates are denoted by $L_x$, $L_y$ and $L_z$, and the lattice widths by $_\Delta x$, $_\Delta y$ and $_\Delta z$.

In this case, in order to obtain the function values of all of the lattice points within the space region, it is necessary to carry out the elementary function computations at least $L_x L_y L_z$ times which corresponds to all lattice points. However, a plurality of elementary functions are actually included in the function $\psi$ in many cases, and in such cases, an even larger number of computations are required.

On the other hand, when making the display, it is necessary to make a visibility judgement, that is, to carry out a hidden line processing (or algorithm) or a hidden surface processing (or algorithm). For this reason, it is necessary to calculate the differential function values of the space coordinates of the multivariable functions in the formula (1) described above. The differential function values indicate the components of the normal vectors perpendicular to an isoplethic surface in the function described by the formula (1), and can be used by obtaining inner products of the normal vectors and the vector which indicates the direction of the line of sight in the visibility judgement.

FIG. 1 is a diagram for explaining the visibility judgement. In FIG. 1, a cross section 11 corresponds to a cross sectional diagram of the isoplethic surface of the multivariable function. Also shown in FIG. 1 are a first normal vector 12 on the isoplethic surface, a second normal vector 13 on the isoplethic surface, and an eyes vector 14 indicating the direction of the line of sight.

The formulas of the differential functions in the formula (1) can be described by the following formulas (2).

$$\frac{\partial \psi}{\partial x} = \psi'_x = \sum_{i=1}^{N} c_i \frac{df_i}{dx} g_i(y) h_i(z) \quad (2)$$

$$\frac{\partial \psi}{\partial y} = \psi'_y = \sum_{i=1}^{N} c_i f_i(x) \frac{dg_i}{dy} h_i(z)$$

$$\frac{\partial \psi}{\partial z} = \psi'_z = \sum_{i=1}^{N} c_i f_i(x) g_i(y) \frac{dh_i}{dz}$$

In other words, the visibility judgement is made depending on whether the inner product of the eyes vector and the normal vector is positive or negative. The visibility is detected if the inner product of the first normal vector 12 and the eyes vector 14 is negative. On the other hand, the invisibility is detected if the inner product of the second normal vector 13 and the eyes vector 14 is positive.

In this case, similarly as in the case of the formula (1), it is necessary to calculate the differential function values at all of the lattice points within the three-dimensional space region. This means that at least $3L_x L_y L_z$ elementary computations must be made, which corresponds to three times the number of all lattice points.

However, if the number of lattice points is increased by the external input means when making the molecular design in order to display a more precise image of the molecular information which is obtained by the theoretical chemical calculations, the number of computations increases by 8 times if the number of lattice points per side is doubled, that is, increases by $2^3$ (to the third power). This is because the number of computations in the multivariable functions, the single variable functions within the multivariable function, and the differential functions used for the visibility judgement is proportional to the number of all lattice points. As a result, there is a problem in that a long calculation time is required until the visibility judgement can be made, thereby deteriorating the operational characteristic of the system. More particularly, the functions become much more complex and an even larger number of elementary function computations become necessary if the number of molecules being treated correspond to greater than ten to several tens of atoms, and there is a problem in that an extremely long calculation time is required.

SUMMARY OF THE INVENTION

Accordingly, it is a general object of the present invention to provide a novel and useful function processing system in which the problems described above are eliminated.

Another and more specific object of the present invention is to provide a function processing system for processing functions to make a three-dimensional display on a screen of a display means by connecting a plurality of lattice points of a space coordinate in a three-dimensional space region, comprising computing means for computing a function value at each of the lattice points by a multivariable function having the space coordinate as an independent variable, where the computing means replaces the multivariable function by a product of a predetermined number of single variable functions and computing each of the single variable functions in advance so that the multivariable function is computed based on function values of each of the single variable functions, and storage means, coupled to the computing means, for storing the function values of the single variable functions which are computed in advance by the computing means. The computing means reads the stored function values of the single variable functions from the storage means when computing the multivariable function. According to the function processing system of the present invention, it is possible to considerably reduce the calculation time because no elementary function is included in the computations which are carried out to obtain the space coordinate of each lattice point in the three-dimensional space. For this reason, it is possible to improve the operability of the function processing system.

Other objects and further features of the present invention will be apparent from the following detailed description when read in conjunction with the accompanying drawings.

DESCRIPTION OF THE PREFERRED EMBODIMENTS

Figure 2:
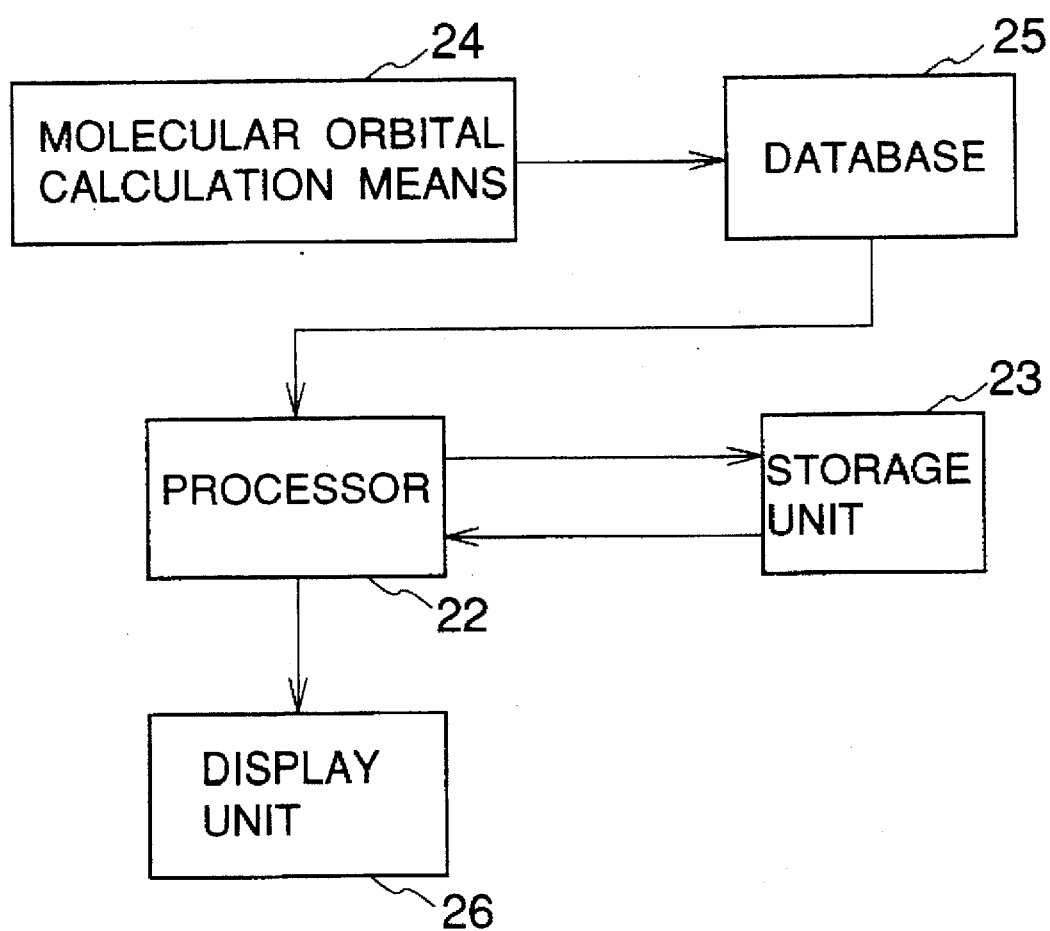
FIG. 2 is a system block diagram showing an essential part of a first embodiment of a function processing system according to the present invention.

FIG. 2 shows the construction of an essential part of a first embodiment of a function processing system according to the present invention. A function processing system 21 shown in FIG. 2 includes a processor 22, a storage unit 23, a molecular orbital calculation means 24, a database 25, and a display unit 26 which are coupled as shown. The processor 22, the molecular orbital calculation means 24 and the database 25 form a computation means.

As will be described later, the processor 22 computes the multivariable functions, the single variable functions, the differential functions and the like when making the theoretical chemical calculations for the molecular design.

The storage unit 23 stores the function values of the N single variable functions of each of the coordinates x, y and z which are calculated in advance by the processor 22, and the differential functions thereof.

The molecular orbital calculation means 24 obtains the constants (C, α will be described later) which are required to compute the molecular orbitals and its energy with the atomic orbital belonging to each atom in the single variable functions calculated by the processor 22. The calculated constants are stored in the database 25.

The display unit 26 makes a three-dimensional display at the lattice points of the three-dimensional space region based on the function values which are obtained by the computations made in the processor 22.

Figure 3:
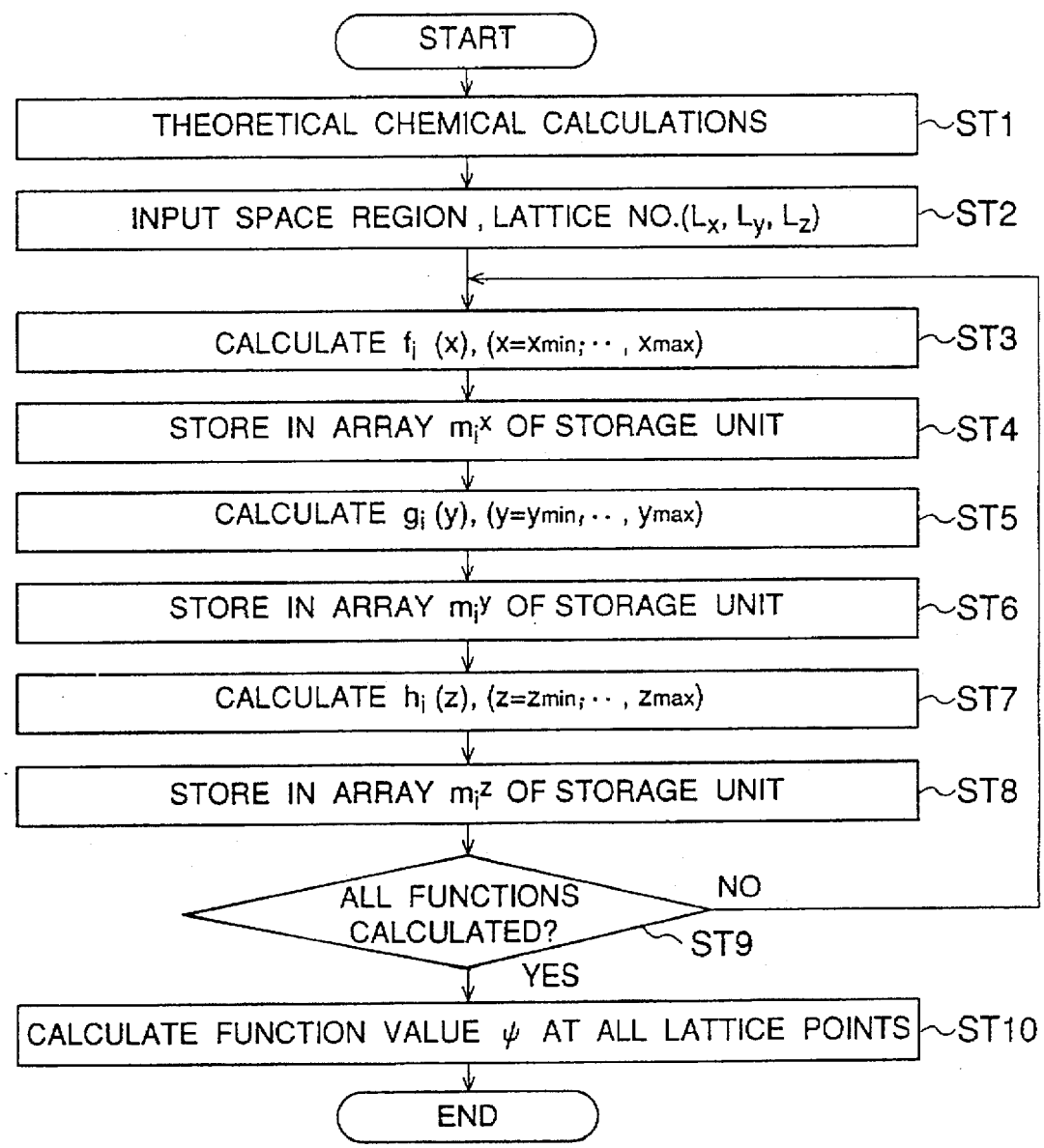
FIG. 3 is a flow chart for explaining a computation process of the first embodiment.

Next, a description will be given of a computation process of the first embodiment, by referring to the flow chart of FIG. 3. In FIG. 3, a step ST1 starts the theoretical chemical calculations. A step ST2 inputs the space region and the lattice number ($L_x$, $L_y$, $L_z$) into the processor 22. Prior to calculating the function $\psi$ of the formula (1) at all of the lattice points, a step ST3 calculates $f_1(x_{min})$, $f_1(x_{min}+\Delta x)$, ..., $f_1(x_{max})$ for each lattice width in the x coordinate in advance, and a step ST4 stores the calculated function values in an array $m_1^x[1]$, $m_1^x[2]$, ..., $m_1^x[L_x]$ in the storage unit 23. In addition, the step ST3 also makes similar calculations with respect to $f_2$, $f_3$, ..., $f_N$, and the step ST4 also similarly stores the calculated function values in arrays $m_2^x$, $m_3^x$, ..., $m_N^x$.

On the other hand, steps ST5 through ST8 calculate $g_i$ and $h_i$ at each lattice point by the processor 22 for the y and z coordinates, and store the calculated function values in arrays $m_i^y$ and $m_i^z$ in the storage unit 23, similarly to the calculations and storage made above for the x coordinate. The calculation of each function such as $f_i(x)$ will be described later. In this case, the number of computations of the elementary functions is $N(L_x+L_y+L_z)$ times, and the capacity of the storage unit 23 required to store the calculated function values is $N(L_x+L_y+L_z)$ words.

Then, a step ST9 decides whether or not the calculations have ended for all of the functions. The process returns to the step ST3 if the decision result in the step ST9 is NO. But if the decision result in the step ST9 is YES, a step ST10 calculates the function value for $\psi$ at all of the lattice points.

For example, if the space coordinate of a three-dimensional lattice point $(l_x, l_y, l_z)$ is denoted by $(x', y', z')$, the value of the function $\psi$ at this point can be obtained from the following formula (3) by using the arrays stored in the memory unit 23.

$$\psi(x',y',z') = \sum_{i=1}^{N} c_i m_i^x[l_x] m_i^y[l_y] m_i^z[l_z] \quad (3)$$

As may be seen from the formula (3) above, the function $\psi$ does not include any computation of elementary functions. For this reason, the value of the function $\psi$ at all of the lattice points can be obtained at an extremely high speed.

Even if the function $\chi$ in the formula (1) cannot be described by the product of single variable functions each made up of the independent variables, it is known in general that the multivariable function can be developed into a linear combination of single variable functions each made up of the variables, as may be seen from the following formula (4).

$$\chi(x,y,z) = \sum_{j=1}^{\infty} c'_j f_j(x) g'_j(y) h'_j(z) \quad (4)$$

Actually, the development of the infinite terms such as those of the formula (4) cannot be processed by the computer. For this reason, if the function $(x, y, z)$ is approximated by M terms, the formula (4) can be rewritten as the following formula (5).

$$\chi(x,y,z) \approx \sum_{j=1}^{M} c'_j f_j(x) g'_j(y) h'_j(z) \quad (5)$$

By substituting the formula (5) into the formula (1), the function $\psi$ can be described by the following formula (6) which has the same form as the formula (1). Hence, the application of this embodiment becomes possible. In the formula (6), $c''_k = c_i c'_j$.

$$\psi(x,y,z) = \sum_{i=1}^{N} \sum_{j=1}^{M} c_i c'_j f_j(x) g'_j(y) h'_j(z) \quad (6)$$
$$= \sum_{k=1}^{N \cdot M} c''_k f_k(x) g'_k(y) h'_k(z)$$

Therefore, The developing region of the formula (6) becomes M times that of the formula (1), and the number of computations required to calculate all of the lattice points becomes $NM(L_x+L_y+L_z)$. This number is considerably small compared to the number of computations $L_x L_y L_z$ which is required according to the conventional system, and it may be seen that this embodiment is extremely advantageous from the point of view of the reducing the required calculation time.

Accordingly, by using the nature that the multivariable functions can be described by the product of single variable functions each made up of the variables or, by a linear combination of the products, and the storing the function values for each lattice width of each of the variables in the storage unit 23 and using the stored function values, it is possible to realize high-speed computations of the function values at all of the lattice points within the three-dimensional space region. Hence, it is possible to obtain the electronic information of the molecule without losing the real-time nature. As a result, the operability of the system using the display unit 26 such as a graphic display unit is improved.

Figure 4:
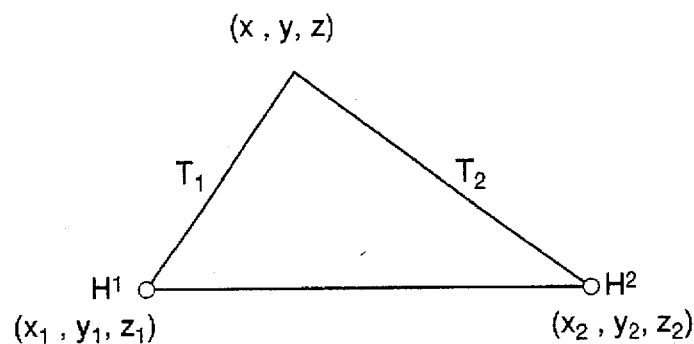
FIG. 4 shows a molecular diagram of a $H_2$ molecule.

Next, a description will be given by taking the $H_2$ molecule as an example. FIG. 4 is a molecular diagram showing the $H_2$ molecule.

If the atoms forming the $H_2$ molecule are denoted by $H^1$ and $H^2$ and the coordinates of these two atoms are respectively denoted by $(x_1, y_1, z_1)$ and $(x_2, y_2, z_2)$, atomic orbitals $\phi_1$ and $\phi_2$ belonging to the respective atoms can be given by the following formulas.

$$\phi_1 = c'_1 G(\alpha_1, r_1) + c'_2 G(\alpha_2, r_1) + c'_3 G(\alpha_3, r_1)$$

$$\phi_2 = c'_4 G(\alpha_4, r_2) + c'_5 G(\alpha_5, r_2) + c'_6 G(\alpha_6, r_2)$$

In this case, $c'_1, c'_2, \ldots, c'_6$ and $\alpha_1, \alpha_2, \ldots, \alpha_6$ are constants which are derived or used in the molecular orbital calculation means 24 as described above. As shown in FIG. 4, $r_1$ and $r_2$ respectively indicate the distance between each atomic nucleus coordinate and an arbitrary coordinate. In addition, the function G is an exponential function described by the following formula.

$$G(\alpha, r) = exp(-\alpha r^2)$$

On the other hand, the molecular orbital $\psi$ can be obtained in the molecular orbital calculation means 24 as a linear combination of the atomic orbitals $\phi_1$, and $\phi_2$. Hence, the molecular orbital $\psi$ can similarly be described by a linear combination with respect to the function G, as may be seen from the following formula.

$$\psi = c''_1 \phi_1 + c''_2 \phi_2$$
$$= c_1 G(\alpha_1, r_1) + c_2 G(\alpha_2, r_1) + c_3 G(\alpha_3, r_1) +$$
$$c_4 G(\alpha_4, r_2) + c_5 G(\alpha_5, r_2) + c_6 G(\alpha_6, r_2)$$

In the above formula $c''_1$, and $c''_2$ are calculated by the molecular orbital calculation means 24 and output to the database 25. In addition, $c_1, c_2, \ldots, c_6$ are used for simplicity and may actually be easily calculated from the product of $c''$ and $c'$.

The following formula (7) can be used to describe $r_\mu$.

$$r_\mu = \sqrt{[(x-x_\mu)^2 + (y-y_\mu)^2 + (z-z_\mu)^2]} \quad , (\mu=1, 2) \quad (7)$$

Hence, the function G can be described by the following formula (8) which is a product of single variable functions each made up of the independent variables.

$$G = (\alpha, r_\mu) \quad (8)$$
$$= G(\alpha, x-x_\mu) G(\alpha, y-y_\mu) G(\alpha, z-z_\mu), (\mu=1, 2)$$

Accordingly, if the lattice space region of the function is defined by $x_{min}$ to $x_{max}$, $Y_{min}$ to $Y_{max}$ and $z_{min}$ to $z_{max}$, the lattice numbers are denoted by $L_x$, $L_y$ and $L_z$, and the lattice widths are denoted by $\Delta x$, $\Delta y$ and $\Delta z$, the computations are made in the processor 22 in the following manner and stored in the arrays $m_i^x$, $m_i^y$ and $m_i^z$ in the storage unit 23 described by the following formulas (9), where $x'_i$, $y'_i$ and $z'_i$ respectively are $x_1$, $y_1$ and $z_1$ when $i=1, 2, 3$ and respectively are $x_2$, $y_2$ and $z_3$ when $i=4, 5, 6$.

$$m_i^x[l_x] = G(\alpha_i, x_{min} + (l_x-1)\Delta x - x'_i)$$

$$m_i^y[l_y] = G(\alpha_i, y_{min} + (l_y-1)\Delta y - y'_i)$$

$m_i^z[l_z]=G(\alpha_i, z_{min}+(l_z-1)\Delta z-z'_i)$ $(i=1,\ldots,6; 1\leq l_x\leq L_x, 1\leq l_y\leq L_y, 1\leq l_z\leq L_z)$ (9)

If the space coordinate of an arbitrary lattice point $(l'_x, l'_y, l'_z)$ is denoted by $(x', y', z')$, the value of the function $\psi$ at this coordinate can be obtained as shown in the following formula (10) using the arrays $m_i^x$, $m_i^y$ and $m_i^z$ stored in the storage unit 23.

$$\psi(x',y',z') = \sum_{i=0}^{6} c_i m_i^x[l'_x]m_i^y[l'_y]m_i^z[l'_z]$$ (10)

When the calculation of the function $\psi$ is made for all of the lattice points within the space region, the calculation can be made at an extremely high speed because the formula (10) does not include the computation of an exponential function.

The following Table 1 shows a comparison of the number of exponential function computations required in this embodiment of the system and the conventional system. As is evident from the Table 1, the effect of reducing the number of computations as compared to the conventional system becomes more notable as the lattice number increases.

TABLE 1

|  | Lattice Number | | |
| --- | --- | --- | --- |
|  | $10^3$ | $50^3$ | $100^3$ |
| No. of Computations in 1st Embodiment | 180 | 900 | 1800 |
| No. of Computations in Conventional System | 6000 | 750000 | 6000000 |
| Ratio to Conventional No. of Computations % | 0.03 | 0.0012 | 0.0003 |

The above described high-speed computation is not only applicable to the case where the multivariable functions are described by the products of the single variable functions each made up of the independent variables. For example, if the atomic orbitals $\phi_1$ and $\phi_2$ are described by the exponential functions of the following formulas (11), it is not possible to make a description in the form of the products of the single variable functions of x, y and z.

$\phi_1=exp(-\zeta_1 r_1)$ $\phi_2=exp(-\zeta_2 r_2)$ $\phi_\mu=f_\mu(x)g_\mu(y)h_\mu(z)$, ($\mu=1, 2$) (11)

However, the high-speed computation described above can easily be applied by developing the formulas (11) by approximation with the function G using the least square method or the like, as shown in the following formula (12). In the formula (12), the degree of approximation of the function becomes higher as the value of n is set to a larger value.

$$\phi_\mu = \sum_{i=1}^{n} C_i G(\alpha_i, r_\mu), (\mu=1, 2)$$ (12)

The constants $C_i$ and $\alpha_i$ are determined in advance of the molecular orbital calculation means 24 by the least square method, for example. More particularly, the constants $C_i$ and $\alpha_i$ can be obtained from the following formulas (13) by obtaining the minimum value for all values of i, where N denotes a normalization constant and r denotes the distance between the coordinates.

$$\int_0^\infty \left(Ne^{-\zeta r} - \sum_j C_j e^{-\alpha_j \cdot r \cdot r}\right)^2 dr = a(C_i, \alpha_i)$$ (13)

Figure 5:
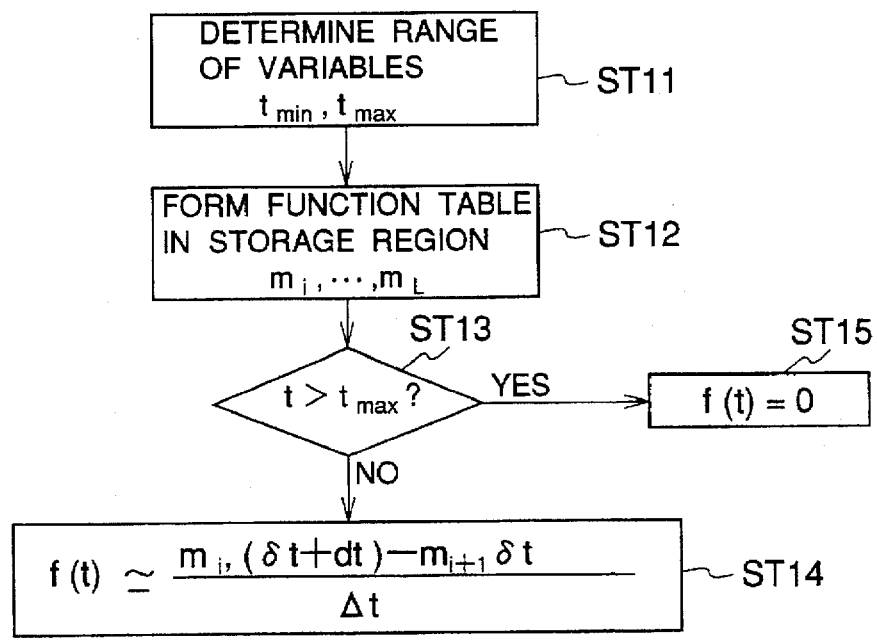
FIG. 5 is a flow chart for explaining a single variable function computation.

$\sum_i \sum_j \int_0^\infty C_i C_j e^{-(\alpha_i+\alpha_j)(\alpha_i+\alpha_j)} dr - 1/2\pi = b(c_i, \alpha_i)$ $A = a + b$ $\frac{\partial A}{\partial d_i} = 0, \frac{\partial A}{\partial c_i} = 0$ Next, a description will be given of the computation of the single variable function described above. FIG. 5 is a flow chart for explaining the single variable function computation. The single variable function is computed by computing the elementary function by a function library which is prepared beforehand similarly to the conventional system. The single variable function is described by exponential functions of the formulas (11) and (12), and the function values are stored in the storage unit 23 as described above. First, a step ST11 sets the range of the variables of the exponential function which is used to $t_{min}$ to $t_{max}$. Hence, if the deviation of the variable is denoted by $\Delta t$, the exponential function is calculated as shown in the following formula (14), and a step ST12 stores the calculated exponential function values in the arrays $m_1, m_2, \ldots, m_{L_t}$ of the storage unit 23 in the form of an exponential function table, where $L_t=(t_{max}-t_{min})/\Delta t+1$.

$m_i=exp(-(t_{min}+(i-1)\Delta t))$, $(1\leq i\leq L_t)$ (14)

If a step ST13 decides that $t<t_{max}$ for $t=\zeta,Y$, a step ST14 obtains the round number of the exponential function in the formula (14) by linear interpolation using two exponential function values of the exponential function table, as shown in the following formula (15).

$f(t)=exp(-t)=[m_l(\delta t+dt)-m_{l+1}\delta t]/\Delta t$ (15)

In the formula (15), 1 is an integer, and 1 and $t_1$ are given by the following formulas.

$l = (t - t_{min})/\Delta t + 1$
$t_l = t_{min} + (l - 1)\Delta t$
$\delta t = t - t_l$ On the other hand, if the step ST13 decides that $t>t_{max}$, a step ST15 sets f(t) to f(t)=0.

As may be seen from the formula (15), the round number of the exponential function is obtained by simple addition, subtraction, multiplication and division without directly calculating the exponential function. As a result, the function $\Phi$ at the lattice points can be calculated at a high speed.

The round number of an exponential function having a higher accuracy can be obtained by increasing the item numbers of the exponential function table, that is, by using a larger table.

In addition, in order to improve the accuracy using the same number of items in the exponential function table, a spline function which is a kind of interpolation method is formed from the exponential function table, and the spline function value is calculated. The spline function employs the multivariable function in each small section when the entire curve is divided into a number of small sections, so that the small sections are connected as smoothly as possible as a whole.

For example, if a third order spline function is formed from the exponential function table, each section of the exponential function table is connected by a different third order function. Hence, the coefficients of the third order functions are calculated in advance from the exponential function table, and the coefficients are stored in the arrays $c_{1,i}$, $c_{2,i}$, $c_{3,i}$ ($i=1, \ldots, L_r-1$) of the storage unit 23.

By using the above arrays $c_{1,i}$, $c_{2,i}$, $c_{3,i}$, the round number of the exponential function of the formula (12) can be obtained from the following formula (16).

$$exp(-t)=m_1+\delta t(c_{1,l}+\delta t(c_{2,l}+\delta t c_{3,l})) \qquad (16)$$

In the formula (16), l, $t_l$ and $\delta t$ can be obtained from the formulas described above with respect to the step ST14.

In the formulas (11) and (12), the relation $\zeta_i \geq 0$ always holds. In addition, a distance $r_i = \sqrt{[(x-x_i)^2+(y-y_i)^2+(z-z_i)^2]}$ is $r_i \geq 0$, and t takes a minimum value for $r \to 0$. Hence, $t_{min}$ in the range of the variables becomes $t_{min}=0$.

Figure 6:
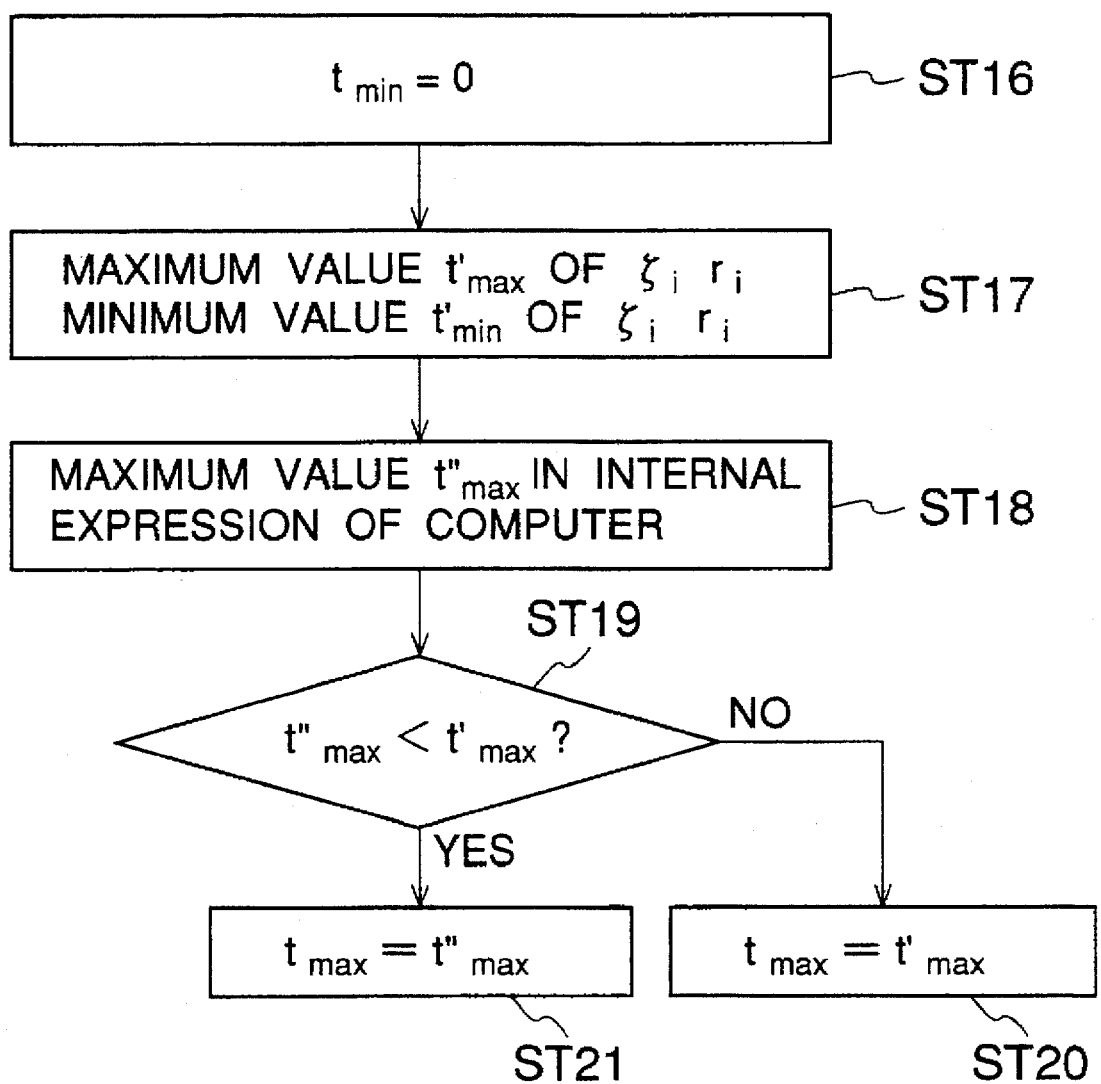
FIG. 6 is a flow chart for explaining the determination of $t_{max}$ of the range of the variables.

FIG. 6 is a flow chart for explaining the determination of $t_{max}$ in the range of the variables. If a step ST16 sets a positive floating point value which is closest to 0 and can be treated in the computer is set to $f_{min}$ ($t_{min}=0$), a step ST17 obtains $t'_{max}$ from the formula (15) as follows.

$$exp(-t'_{max})=f_{min}$$

$$t'_{max}=\log_e f_{min}$$

Generally, the internal representation of the floating point differs among the kinds of computers, and the value of $t'_{max}$ accordingly differs.

Next, a step ST18 calculates $\zeta_i r_i$ for the 8 coordinates corresponding to the vertexes of the space region with respect to all $\zeta_i$ within the formula (15), and sets the maximum calculated value to $t''_{max}$. Furthermore, a step ST19 compares $t'_{max}$ and $t''_{max}$ to decide whether or not $t''_{max} < t'_{max}$. A step ST20 is carried out if the decision result in the step ST19 is NO, and a step ST21 is carried out if the decision result in the step ST19 is YES. In other words, the smaller of the two values $t'_{max}$ and $t''_{max}$ is set as $t_{max}$.

By this process, the surplus information which is not used for the actual exponential function calculation is removed from the exponential function table if $t'_{max} > t''_{max}$, so that the storage capacity of the storage unit 23 can be used effectively. In addition, if $t'_{max} < t''_{max}$, the variable exceeds $t_{max}$ in the exponential function calculation, and the formulas (15) and (16) cannot be applied. However, an underflow will occur even in the actual exponential calculation, and the round number of the exponential function can be regarded as 0.

Accordingly, with respect to the function which includes a large number of exponential functions, the function values obtained by intermittently varying the variables are stored in advance within the storage unit 23 in the form of the exponential function table, and the actual exponential function values are calculated through interpolation using the exponential function table. For this reason, it is possible to obtain the round values of the exponential functions at a high speed, thereby making it possible to also calculate at a high speed the function which includes a large number of exponential functions.

If the $H_2$ molecule is taken as an example, similarly as in the above described case, the function described by the following formula is calculated with respect to the entire region of a certain space region for this $H_2$ molecule.

$$\psi=c_1 exp(-\zeta_1 r_1)+c_2 exp(-\zeta_2 r_2)$$

In this formula, $c_1$ and $c_2$ can be obtained from the theoretical chemical calculations. In addition, $\zeta_1$ and $\zeta_2$ are determined prior to making the theoretical chemical calculations. $r_1$ and $r_2$ respectively denote the distances between the coordinate (x, y, z) and $H^2$ and $H^1$ in FIG. 4.

In this case, when compared to the conventional system, the calculation time with respect to a certain space region is 0.64 times in the case of the linear interpolation and 0.75 times for the spline interpolation.

Figure 1:
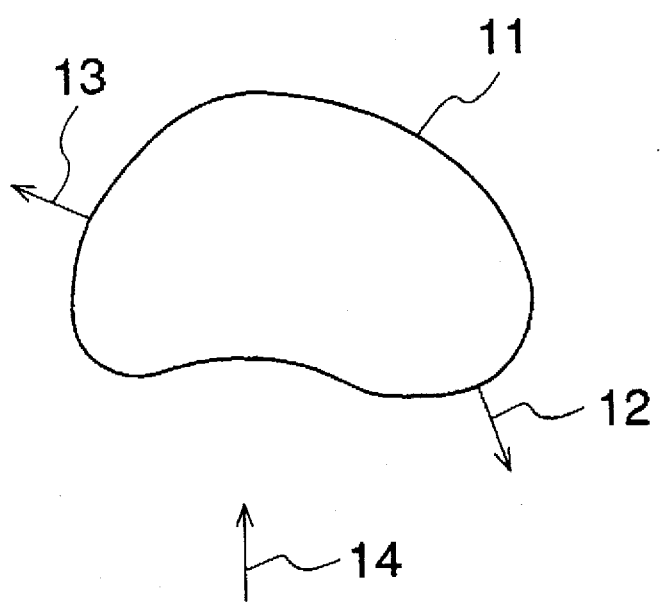
FIG. 1 is a diagram for explaining the visibility judgement.
Figure 7:
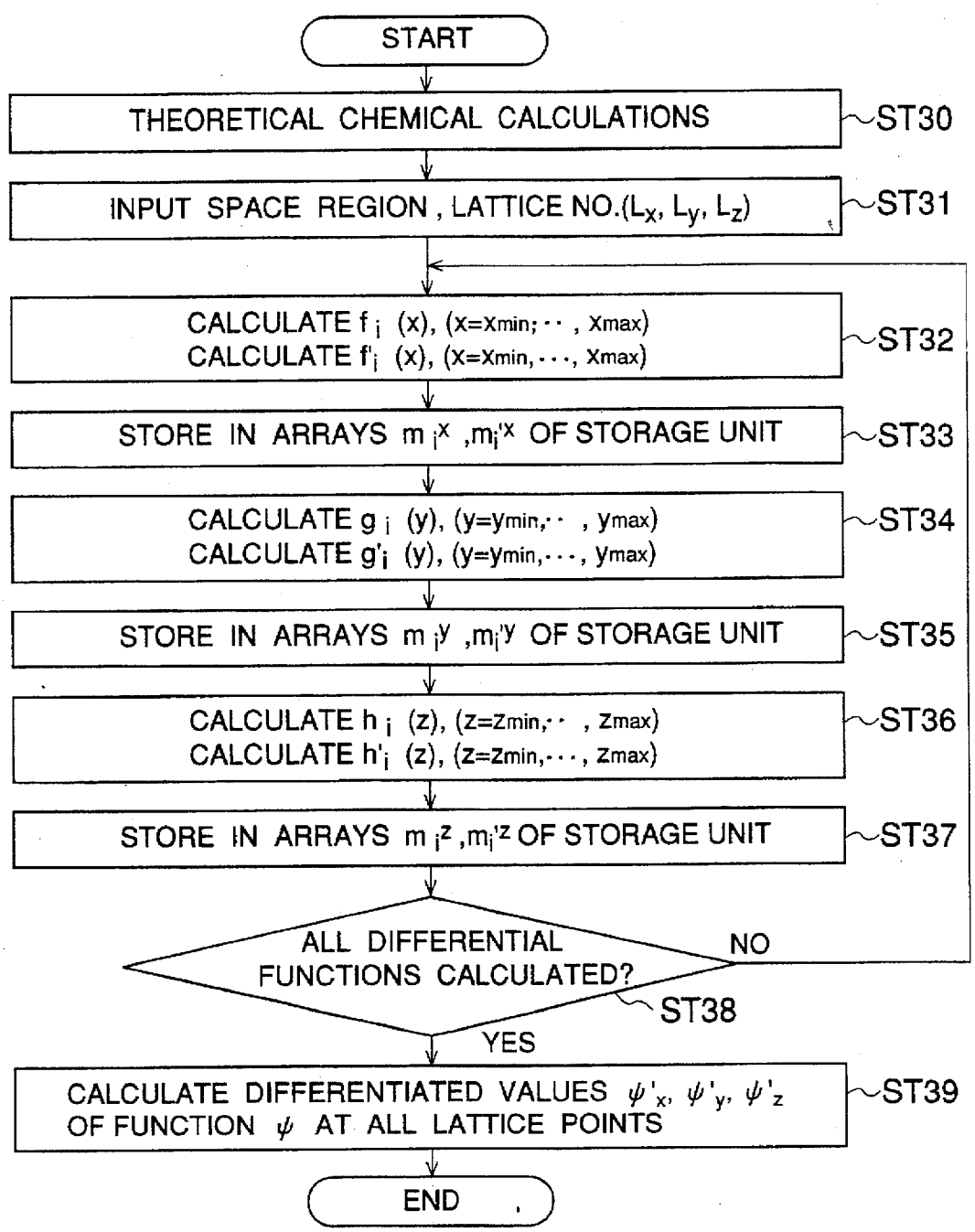
FIG. 7 is a flow chart for explaining a visibility computation.

Next, a description will be given of the computation related to the visibility judgement. FIG. 7 is a flow chart showing the visibility computation. As described above with reference to FIG. 1, it is necessary to carry out the hidden line processing and the hidden surface processing in order to make the display. In other words, it is necessary to compute the differential functions of the formula (2) described above.

In this embodiment, the multivariable function is described by the product of the single variable functions, as described above. Hence, the function values of the single variable functions and the function values of the differential functions are calculated and stored in advance within the storage unit 23.

In other words, in FIG. 7, a step ST30 starts the theoretical chemical calculations, and a step ST31 inputs the space region and the lattice number ($L_x$, $L_y$, $L_z$) into the processor 22, similarly to the case shown in FIG. 3.

Next, a step ST32 calculates in advance $f_1(x_{min})$, $f_1(x_{min}+\Delta x), \ldots, f_1(x_{max})$ for each lattice width in the x coordinate by the processor 22, and also makes similar calculations for $f_2, f_3, \ldots, f_N$. In addition, the step ST32 also calculates the differential values $f_i'(x)=df_i/dx$. A step ST33 stores the values calculated in the step ST32 in the arrays $m_1^x(m_1^x[1], m_1^x[2], \ldots, m_1^x[L_x])$, $m_2^x, M_3^x, \ldots, M_n^x$ and $M_1^{'x}, M_2^{'x}, M_3^{'x}, \ldots, M_n^{'x}$ within the storage unit 23.

Similarly, steps ST34 through ST37 calculate $g_i$ and $h_i$, and $g_i'$ and $h_i'$ for each lattice point in the y and z coordinates, and the calculated values are stored in the arrays $m_i^y$ and $m_i^z$, and $m_i^{'y}$ and $m_i^{'z}$.

The steps ST32 through ST37 are repeated until the calculations are made for all of the lattice points. More particularly, a step ST38 decides whether or not all of the differential functions have been calculated, and the process returns to the step ST32 if the decision result in the step ST38 is NO. On the other hand, if the decision result in the step ST38 is YES and the storage of all of the necessary values in the storage unit 23 has ended, a step ST39 calculates differentiated values $\psi'_x$, $\psi'_y$ and $\psi'_z$ of the function $\psi$ at all of the lattice points.

The number of the above computations of the elementary functions is $2N(L_x+L_y+L_z)+L+Lz$ times, and the required storage capacity of the storage unit 23 is $2N(L_x+L_y+L_z)+L_z$ words.

Therefore, by making the computations of the required elementary functions and storing the computed values into the storage unit 23 in advance, and if the space coordinate of the three-dimensional lattice point described by ($l_x, l_y, l_z$) is represented by (x, y, z), for example, the values of the differential function $\psi'$ related to each of the coordinates x, y and z of the function $\psi$ at this point can be obtained from the following formulas (17) using the arrays in the storage unit 23.

$$\psi'_x(x,y,z) = \sum_{i=1}^{N} c_i m_i^{'x}[l_x] m_i^x[l_y] m_i^z[l_z] \qquad (17)$$

$$\psi'_y(x,y,z) = \sum_{i=1}^{N} c_i m_i^x[l_m] m_i^{'x}[l_x] m_i^{'y}[l_y] m_i^z[l_z]$$

-continued $$\psi'_z(x,y,z) = \sum_{i=1}^{N} c_i m_i^x[l_x] m_i^y[l_y] m_i^z[l_z]$$

The above formulas (17) do not include any computation of the elementary function. For this reason, the value of the differential function of the function $\psi$ at all of the lattice points can be obtained at an extremely high speed when compared to the conventional system.

In the case where the above function $\chi$ cannot be described by the product of the single variable functions each made up of the independent variables, this embodiment can be applied similarly as described above with reference to the formulas (4) through (6). Accordingly, the differential functions related to the space coordinate can be described by the following formulas (18), similarly to the formulas (2) described above, where $C'_k = c_i C_j$ in the formulas (18).

$$\frac{\partial \psi}{\partial x} = \sum_{k=1}^{NM} C'_k \frac{dF_k}{dx} G_k(y) H_k(z) \quad (18)$$

$$\frac{\partial \psi}{\partial y} = \sum_{k=1}^{NM} C'_k F_k(x) \frac{dG_k}{dy} H_k(z)$$

$$\frac{\partial \psi}{\partial z} = \sum_{k=1}^{NM} C'_k F_k(x) G_k(y) \frac{dH_k}{dz}$$

Compared to the formulas (2), the number of developing terms is M times in the formulas (18). Hence, in order to calculate the differential function values at all of the lattice points, it is necessary to make the computations $2NM(L_x+L_y+L_z)$ times. However, this number $2NM(L_x+L_y+L_z)$ is considerably small compared to the number $3L_xL_yL_z$ which is required in the conventional system, and this embodiment is much more advantageous from the point of view of the required calculation time.

Therefore, by utilizing the nature that the multivariable functions can be described by the products of the single variable functions each made up of independent variables or, the linear combinations of these products, and storing in the storage unit 23 the function values and the differential function values for each lattice width of each variable, it becomes possible to realize a high-speed computation of the differential function value at all of the lattice points within the three-dimensional space region by using the stored values.

If the $H_2$ molecule shown in FIG. 4 is taken as an example, the terms $m_i^x[l_x]$, $m_i^y[l_y]$ and $m_i^z[l_z]$ of the formulas (9) are differentiated so as to obtain the following formulas (19) which are then stored in the arrays $m_i^{'x}$, $m_i^{'y}$ and $m_i^{'z}$ within the storage unit 23.

$$m_i^{'x}[l_x] = G'(a_i, x_{min}+(l_x-1)\Delta x - X_i)$$

$$m_i^{'y}[l_y] = G'(a_i, y_{min}+(l_y-1)\Delta y - Y_i)$$

$$m_i^{'z}[l_z] = G'(a_i, z_{min}+(l_z-1)\Delta z - Z_i)$$

$$(i=1, \ldots, 6;\ 1 \leq l_x \leq L_x,\ 1 \leq l_y \leq L_y;\ 1 \leq l_z \leq L_z) \quad (19)$$

In the formulas (19) above, $X_i$, $Y_i$ and $Z_i$ respectively are $x_1$, $y_1$ and $z_1$ when $i=1, 2, 3$ and are $x_2$, $y_2$ and $z_2$ when $i=4, 5, 6$. In addition, G' is a differential function of the function G and is described by the following formula.

$$G'(\alpha,r) = dG(\alpha,r)/dr$$

$$= -2\alpha r \exp(-\alpha r^2)$$

$$= -2\alpha r G(\alpha,r)$$

If the space coordinate of an arbitrary lattice point $(l_x, l_y, l_z)$ is denoted by $(X, Y, Z)$, the values of the differential functions $\psi'_x$, $\psi'_y$ and $\psi'_z$ at this coordinate can be obtained from the following formulas (20) using the arrays $m_i^x$, $m_i^y$, and $m_i^{'x}$, $m_i^{'y}$ and $m_i^{'z}$ which are stored in the storage unit 23.

$$\psi'_x(X,Y,Z) = \sum_{i=1}^{6} c_i m_i^{'x}[l_x] m_i^y[l_y] m_i^z[l_z] \quad (20)$$

$$\psi'_y(X,Y,Z) = \sum_{i=1}^{6} c_i m_i^x[l_x] m_i^{'y}[l_y] m_i^z[l_z]$$

$$\psi'_z(X,Y,Z) = \sum_{i=1}^{6} c_i m_i^x[l_x] m_i^y[l_y] m_i^{'z}[l_z]$$

When the function $\psi$ is calculated for all of the lattice points within the space region, the calculation can be made at an extremely high speed because the above formulas (20) do not include computations of the exponential functions.

The following Table 3 shows a comparison of the number of exponential function computations required in this embodiment of the system and the conventional system. As is evident from the Table 2, the effect of reducing the number of computations as compared to the conventional system becomes more notable as the lattice number increases.

TABLE 2

|  | Lattice Number | | |
| --- | --- | --- | --- |
|  | $10^3$ | $50^3$ | $100^3$ |
| No. of Computations in 1st Embodiment | 360 | 1800 | 3600 |
| No. of Computations in Conventional System | 18000 | 2250000 | 18000000 |
| Ratio to Conventional No. of Computations % | 0.02 | 0.0008 | 0.0002 |

In this embodiment, the present invention is applied to the molecular design support system. However, the present invention is of course applicable to all computations which are carried out to make a three-dimensional display on the three-dimensional space region of the display unit.

In order to display an image which is realistic, it is essential to carry out the hidden line processing with respect to the object which is to be displayed, and various methods of hidden line processing have been proposed. For example, in the case of a solid model display, there is the so-called Z-buffer method. The Z-buffer method stores in the storage unit the depth coordinate of the image which is to be displayed and the brightness/luminance at that point depending on the resolution of the display unit. However, according to this Z-buffer method, the storage unit must have a large storage capacity if the image is to be displayed with a large resolution. In addition, the display is limited to the solid model, and cannot be applied to the display of a wire frame model.

Furthermore, the system of the first embodiment which replaces the multivariable functions as linear combinations of the products of single variable functions so as to carry out the computations at a high speed cannot be applied as it is to the hidden line processing, because in a coordinate system which has an axis in the direction of the line of sight of the operator a rotation of the coordinate system is involved.

In order to carry out a hidden line processing which is applicable to various models, it is necessary to calculate the function values in the coordinate system which has an axis in the direction of the line of sight of the operator, in addition to calculating the function values in the coordinate system of the molecule. However, it takes an extremely long calculation time to make such calculations of the complex functions which are obtained from the result of the molecular orbital calculation or the like. For this reason, in the molecular design support system which requires real-time processing, it is virtually impossible to display real functions in real-time.

In view of the above, a second embodiment of the function processing system according to the present invention takes the following measures when displaying electronic information of the molecules on the display unit, so as to enable real-time processing and improve the operability of the system. That is, the multivariable functions are replaced by linear combinations of products of single variable functions, and a linear transformation is made using a unitary transformation unit depending on the function form of the linear combination coefficients of the elementary functions forming the functions. As a result, it becomes possible to compute at a high speed the function values in the coordinate system which has an axis in the direction of the line of sight of the operator.

On the other hand, a third embodiment of the function processing system according to the present invention takes the following measures when displaying electronic information of the molecules on the display unit, so as to enable real-time processing and improve the operability of the system. That is, the multivariable functions are replaced by linear combinations of products of single variable functions, and the function values at the three-dimensional lattice points are calculated at a high speed. In addition, the function values in the coordinate system which has an axis in the direction of the line of sight of the operator are replaced by predicted values which are obtained from the function values at the lattice points in the coordinate system obtained above through interpolation. For example, the multivariable functions are scalar functions or vector functions.

In order to judge the visibility of a point on the isoplethic surface where the multivariable function $\psi(x, y, z)=a$ (constant), a scalar product of unit vectors of the normal vector (gradient) of the surface which includes this point and the direction of the line of sight (eyes vector) is obtained, and the invisibility is detected if the scalar product is greater than or equal to 0. If the scalar product is negative, the function values are further calculated along the direction of the line of sight of the operator, so as to determine whether or not an obstructing surface (other isoplethic surface which hides this point) exists. The visibility is detected only when no obstructing surface exists.

Figure 8:
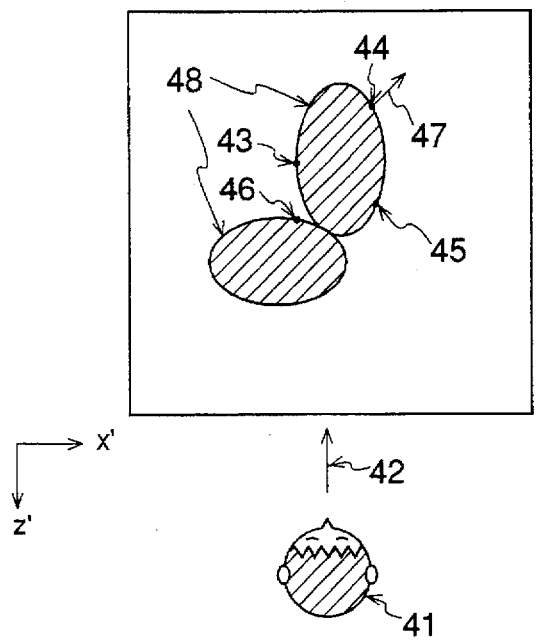
FIG. 8 is a diagram for explaining a particular example of the visibility judgement.

FIG. 8 is a diagram for explaining a particular example of the visibility judgement. In FIG. 8, a normal vector 47 at a point 44 on an isoplethic surface 48 is invisible, because the inner product of the normal vector 47 and an eyes vector 42 becomes greater than or equal to 0. On the other hand, the inner product of the normal vector and the eyes vector becomes negative for both points 43 and 45 on the isoplethic surface 48, but the point 43 becomes invisible because there exists a point 46 which intersects another isoplethic surface in front when viewed from an operator 41.

Figure 9:
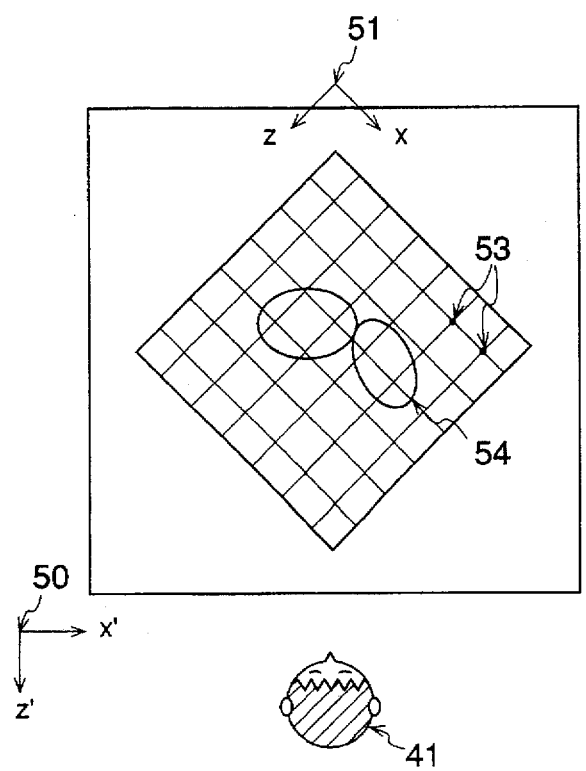
FIG. 9 is a diagram for explaining the case where the coordinate systems of the operator and a plotted object differ.

The calculation of the function values along the direction of the line of sight of the operator can be made at a high speed by replacing the multivariable functions by the linear combination of the products of the single variable functions as in the case of the first embodiment, if the direction of the line of sight matches one axis of the coordinate system of the multivariable function. However, if the direction of the line of sight does not match one axis of the coordiate system of the multivariable function as shown in FIG. 9, such as the case where the isoplethic surface of the multivariable functions is rotated, it is impossible to apply the high-speed computations of the first embodiment as they are. In FIG. 9, an X'-coordinate system 50 has an axis in the direction of the line of sight of the operator 41 with respect to the screen of the display unit 26, and a X-coordinate system 51 is the coordinate system of the multivariable function. A lattice point 53 is an example of the lattice point in the coordinate system 51, and an isoplethic surface ($\psi=a$) is denoted by a reference numeral 54.

The high-speed computations of the first embodiment cannot be applied as they are for the following reasons.

That is, if it is assumed that the multivariable function $\psi$ in the coordinate system X can be replaced by the linear combination of the products of the single variable functions as shown in the following formula (21), $$\psi(x,y,z) = \sum_i d_i f_i(x) g_i(y) h_i(z) \qquad (21)$$

the multivariable function $\psi$ described by the coordinate system X' having a z-axis in the direction of the line of sight of the operator can be written as X'=UX, and the coordinate system X' is subjected to a unitary transformation by the coordinate system X. For this reason, the multivariable function $\psi$ in the formula (21) above normally cannot be replaced by a linear combination of the products of the single variable functions if described in the coordinate system X'.

However, the second embodiment takes notice that, if the multivariable function $\psi$ which is often used in the molecular orbital calculation or the like can be described by the following formula (22)

$$\psi(x,y,z) = \sum_i c_i \chi(x,y,z)$$

and $\chi$ can be described by the following formula, $$\chi(x, y, z) = (x-x_i)^{Nx}(y-y_i)^{Ny}(z-z_i)^{Nz} exp(-\alpha|r-r_i|^2)$$

the multivariable function $\psi$ can be replaced by a product of single variable functions of the coordinate system X' as shown in the following formula (23).

$$\psi(x', y', z') = \sum_i c_i' f_i'(x') g_i'(y') h_i'(z') \qquad (23)$$

In the formula (23) above, $c_i'$ is obtained by carrying out a unitary transformation depending on the form of the function, as will be described later. In addition, in the formula (23), $f_i'$, $g_i'$ and $h_i'$ can respectively be described by the following formulas.

$$f_i'(x') = (x'-x_i')^{Nx} exp(-\alpha(x'-x_i')^2)$$

$$g_i'(y') = (y'-y_i')^{Nx} exp(-\alpha(y'-y_i')^2)$$

$$h_i'(z') = (z'-z_i')^{Nx} exp(-\alpha(z'-z_i')^2)$$

Further, if the following functions $$\chi_{P,x} = (x-x_i) exp(-\alpha|r-r_a|^2)$$

$$\chi_{P,y} = (y-y_i) exp(-\alpha|r-r_a|^2)$$

$\chi_{Pz} = (z-z_i)\exp(-\alpha|r-r_i|^2)$ are included in the formula (22) and the respective linear combination coefficients are denoted by $c_P=(c_{Px}, c_{Py}, c_{Pz})$, a linear combination coefficient $c_P'$ in the coordinate system X' can be obtained in the following manner using a unitary transformation unit 67 shown in FIG. 10 which will be described later.

$$c_P' = Uc_P$$

In addition, if the formula (22) includes the following functions $\chi d_{xx} = (x-x_i)^2 \exp(-\alpha|r-r_i|^2)$ $\chi d_{xy} = (x-x_i)(y-y_i)\exp(-\alpha|r-r_i|^2)$ $\chi d_{yy} = (y-y_i)^2 \exp(-\alpha|r-r_i|^2)$ $\chi d_{yz} = (y-y_i)(z-z_i)\exp(-\alpha|r-r_i|^2)$ $\chi d_{zz} = (z-z_i)^2 \exp(-\alpha|r-r_i|^2)$ $\chi d_{zx} = (z-z_i)(x-x_i)\exp(-\alpha|r-r_i|^2)$ a linear combination coefficient $c_d$ is transformed in the following manner similarly using the unitary transformation unit 67.

$$c_d' = UUc_d$$

Generally, if there exists a function group related to the above $\chi(x, y, z)$ and having the same value for $N_x+N_y+N_z$, a linear combination coefficient c is transformed in the unitary transformation unit 67 as follows.

$$c' = U^{(Nz+Ny+Nz)} c$$

Therefore, the linear combination coefficient c is partially transformed in the unitary transformation unit 67 depending on the form of the function, so as to calculate the new linear combination coefficient c'. This new linear combination coefficient c' is stored in an array cp within the storage unit 23 shown in FIG. 10 prior to the hidden line processing.

Next, the values of $f_i'$, $g_i'$ and $h_i'$ in the formula (23) are calculated for the three-dimensional lattice points of the coordinate system X'. In other words, $f_i'(x')$, $x'=x_{min}, x_{min}+\Delta x, \ldots, x_{max}$ are calculated and stored in the array $M_x$ within the storage unit 23. Similarly, $g_i'(y')$ and $h_i'(z')$ are calculated and stored in the arrays $M_y$ and $M_z$ within the storage unit 23.

Actually, the judgement as to whether the point $(x_O', y_O', z_O')$ on an isoplethic surface is visible is made in the following manner using the arrays cp, $M_x$, $M_y$ and $M_z$ stored in the storage unit 23 after calculating the inner product of the eyes vector and the normal (gradient) on the isoplethic surface as described above and the calculated inner product is negative, that is, when it is found that the surface is facing the operator.

First, a lattice point on the xy plane of the coordinate system X' and closest to $(x_O', y_O')$ is obtained and regarded as $(x_G', y_G')$. The xy plane is a surface which is perpendicular to the direction of the line of sight of the operator. Then, a lattice point which is in front of $z_O'$, that is, on the operator side, and is closest to $z_O'$ is obtained and regarded as $z_G'$.

Next, the following formula (24) is used to calculate the value of $\psi$ in the direction of the line of sight by varying $z=z_G', z_G'+\Delta z, \ldots, z_{max}$.

$$\psi = \sum_i cp[i] M_x[x_g'][i] M_y[y_G'][i] M_z[z][i] \quad (24)$$

In this case, if the value of $\psi$ traverses another isoplethic surface and $\psi(x_G', y_G', z+N\Delta z) < \alpha < \psi(x_G', y_G', z+(N+1)\Delta z)$ or $\psi(x_G', y_G', z+N\Delta z) > \alpha > \psi(x_G', y_G', z+(N+1)\Delta z)$ stands, it is judged that the point $(x_O', y_O', z_O')$ on the isoplethic surface is invisible.

Accordingly, in this embodiment, it is possible to carry out the hidden line processing with respect to the isoplethic surface of the multivariable functions at a high speed. As a result, it is possible to display the electronic information of the molecule in the molecular design support system, for example, with a satisfactory real-time processing. Hence, the operability of the system using the display unit or the like is improved.

Figure 10:
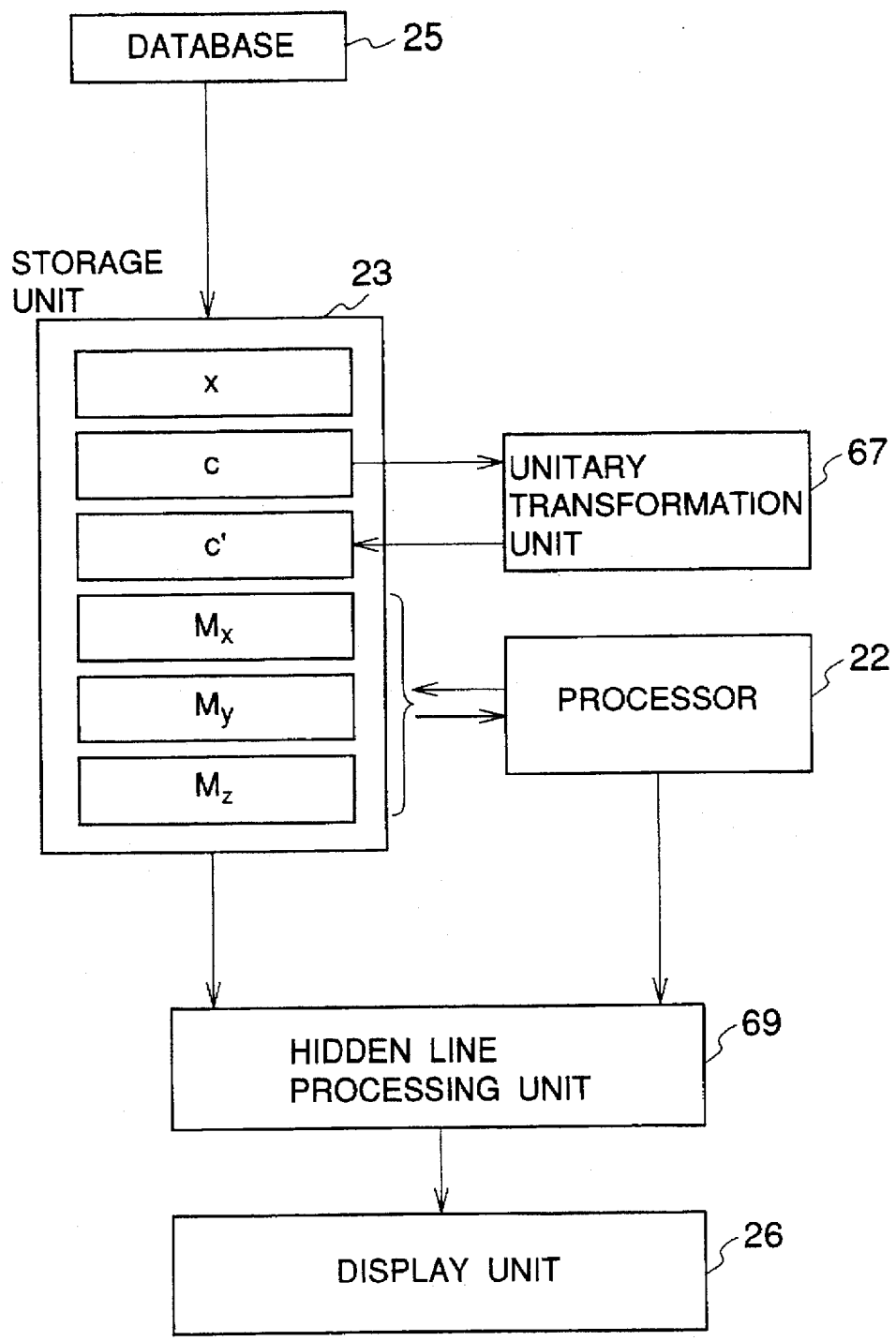
FIG. 10 is a system block diagram showing an essential part of a second embodiment of the function processing system according to the present invention.

FIG. 10 shows the construction of the second embodiment. A function processing system 61 shown in FIG. 10 includes a processor 22, a storage unit 23, a database 25, a display unit 28, a unitary transformation unit 67 and a hidden line processing unit 69 which are connected as shown. The illustration of the molecular orbital calculation means 24 is omitted in FIG. 10.

The unitary transformation unit 67 transforms c into c' based on the linear combination coefficient c and the molecular coordinate system C obtained from the database 25. The new linear combination coefficient c' which is obtained by this transformation is stored in the array cp within the storage unit 23.

Next, the processor 22 calculates $f_i'$, $g_i'$ and $h_i'$ according to the formula (23) described above, and stores the calculated values into the arrays $M_x$, $M_y$ and $M_z$ within the storage unit 23.

Thereafter, the hidden line processing unit 69 carries out the hidden line processing described above, and the function value hunting in the direction of the line of sight of the operator is made at a high speed. Finally, the image which has been subjected to the hidden line processing is displayed on the display unit 23.

Figure 11:
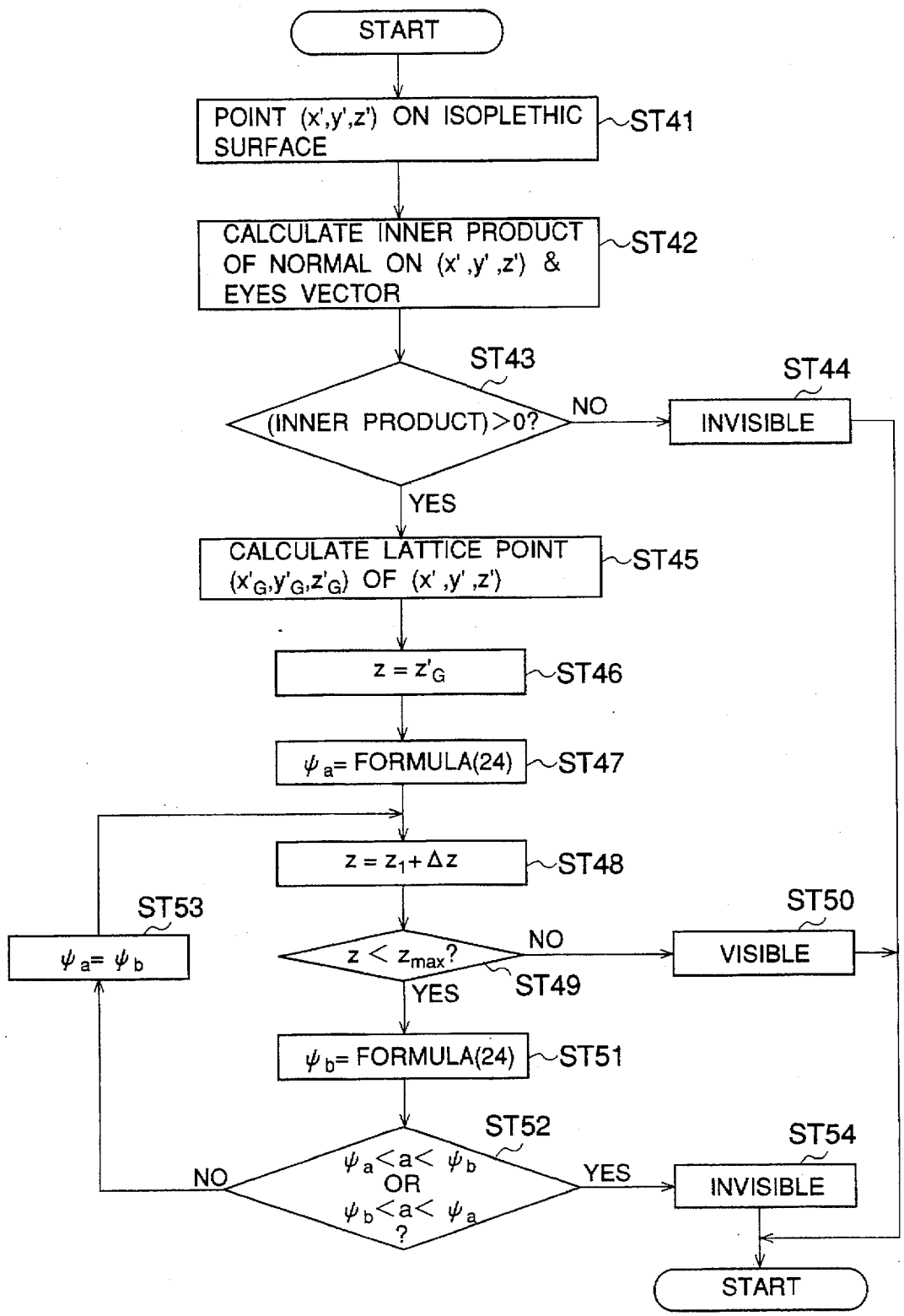
FIG. 11 is a flow chart for explaining the operation of the second embodiment.

FIG. 11 is a flow chart showing the computation process of the embodiment shown in FIG. 10. In FIG. 11, a step ST41 obtains a point (x', y', z') on an isoplethic surface. A step ST42 calculates the inner product of the eyes vector and the normal (gradient) on the isoplethic surface on which the point (x', y', z') is positioned. A step ST43 decides whether or not the value of the calculated inner product is greater than or equal to 0. If the decision result in the step ST43 is NO, a step ST44 judges that this point (x', y', z') is invisible, and the process ends.

On the other hand, if the decision result in the step ST43 is YES, a step ST45 calculates a lattice point $(x_G', y_G', z_G')$ with respect to the point (x', y', z'). A step ST46 sets $z=z_G'$, and a step ST47 calculates $\psi_a$ based on the formula (24) described above. In addition, a step ST48 sets $z=z+\Delta z$.

A step ST49 decides whether or not $z<z_{max}$. If the decision result in the step ST49 is NO, a step ST50 judges that the point (x', y', z') is visible, and the process ends.

On the other hand, if the decision result in the step ST49 is YES, a step ST51 calculates $\psi_b$ based on the formula (24) described above. A step ST52 decides whether or not $\psi_a < a < \psi_b$ or $\psi_b < a < \psi_a$. If the decision result in the step ST52 is NO, a step ST53 sets $\psi_a = \psi_b$, and the process returns to the step ST48. But if the decision result in the step ST52 is YES, a step ST54 judges that the point (x', y', z') is invisible, and the process ends.

Next, a description will be given of the third embodiment of the function processing system according to the present invention.

As described above, the coordinate system X' is subjected to the unitary transformation by the coordinate system X, and if $\psi$ of the formula (21) is described in the coordinate system X', $\psi$ cannot be replaced by a linear combination of the products of the single variable functions except for special cases.

Figure 12:
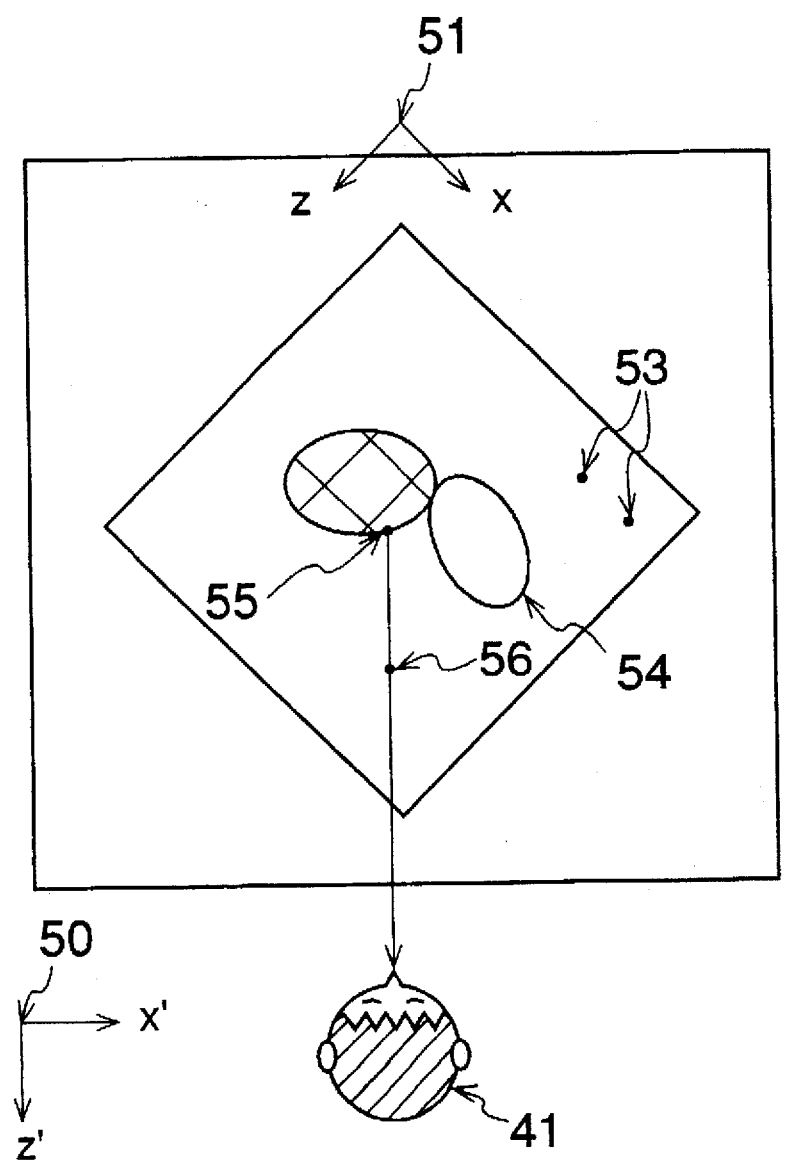
FIG. 12 is a diagram for explaining the case where the coordinate systems of the operator and the plotted object differ in a third embodiment of the function processing system according to the present invention.

Hence, in this third embodiment, a function value of a different point 56 along the direction of the line of sight of the operator 41 is obtained in the following manner with respect to a point 55 on an isoplethic surface shown in FIG. 12. In other words, the coordinate of the point 56 is denoted by $(x_F, y_F, z_F)$, and 4 lattice points in the vicinity of this point 56 is selected. In FIG. 12, those parts which are the same as those corresponding parts in FIG. 9 are designated by the same reference numerals, and a description thereof will be omitted.

The coordinates of the 4 selected lattice points will respectively be denoted by $(x_1, y_1, z_1)$, $(x_2, y_2, z_2)$, $(x_3, y_3, z_3)$ and $(x_4, y_4, z_4)$. In addition, the function values at these 4 selected lattice points will respectively be denoted by $\psi_1$, $\psi_2$, $\psi_3$ and $\psi_4$. Then, coefficients $c_1$, $c_2$, $c_3$ and $c_4$ which will make the following formulas stand are determined.

$$\psi_1 = c_1 x_1 + c_2 y_1 + c_3 z_1 + c_4$$

$$\psi_2 = c_1 x_2 + c_2 y_2 + c_3 z_2 30\ c_4$$

$$\psi_3 = c_1 x_3 + c_2 y_3 + c_3 z_3 + c_4$$

$$\psi_4 = c_1 x_4 + c_2 y_4 + c_3 z_4 + c_4$$

Taking into consideration the fact that the above formulas are linear, the coefficients $c_1$, $c_2$, $c_3$ and $c_4$ can easily be obtained by solving a 4-element simultaneous equation. In other words, an inverse matrix of the following matrix indicated by the formula (25) is actually obtained, $$X = \begin{pmatrix} x_1 & y_1 & z_1 & 1 \\ x_2 & y_2 & z_2 & 1 \\ x_3 & y_3 & z_3 & 1 \\ x_4 & y_4 & z_4 & 1 \end{pmatrix} \quad (25)$$

and a product of this inverse matrix and the following matrix indicated by the formula (26) is obtained.

$$\psi = \begin{pmatrix} \psi_1 \\ \psi_2 \\ \psi_3 \\ \psi_4 \end{pmatrix} \quad (26)$$

A predicted value of the function value $\psi_F$ at the point 56 is obtained by carrying out the following calculation after determining the coefficients $c_1$, $c_2$, $c_3$ and $c_4$.

$$\psi_F = c_1 x_F + c_2 y_F + c_3 z_F + c_4$$

Alternatively, instead of using the above formula, it is also possible to similarly determine the coefficients $c_1, c_2, \ldots$ using the following second order equation.

$$\psi = c_1 x^2 + c_2 y^2 + c_3 z^2 + c_4 xy + c_5 yz + c_6 zx + c_7 x + c_8 y + c_9 z + c_{10} +$$

In this case, it is necessary to select 10 lattice points in the vicinity of the point 56, but a more accurate predicted value can be obtained although the calculation time becomes longer than the above case where the first order equation is used.

The above described operation is also applicable to third, fourth, . . . order equations, however, the higher the order of the equation, the larger the required information related to the lattice points in the vicinity of the point 56 becomes and the longer the calculation time becomes. For this reason, it is desirable to select the order of the equation to a suitable value.

According to this embodiment, it is also possible to carry out the hidden line processing with respect to the isoplethic surface of the multivariable functions at a high speed. As a result, it is possible to display the electronic information of the molecule in the molecular design support system, for example, with a satisfactory real-time processing. Hence, the operability of the system using the display unit or the like is improved.

Figure 13:
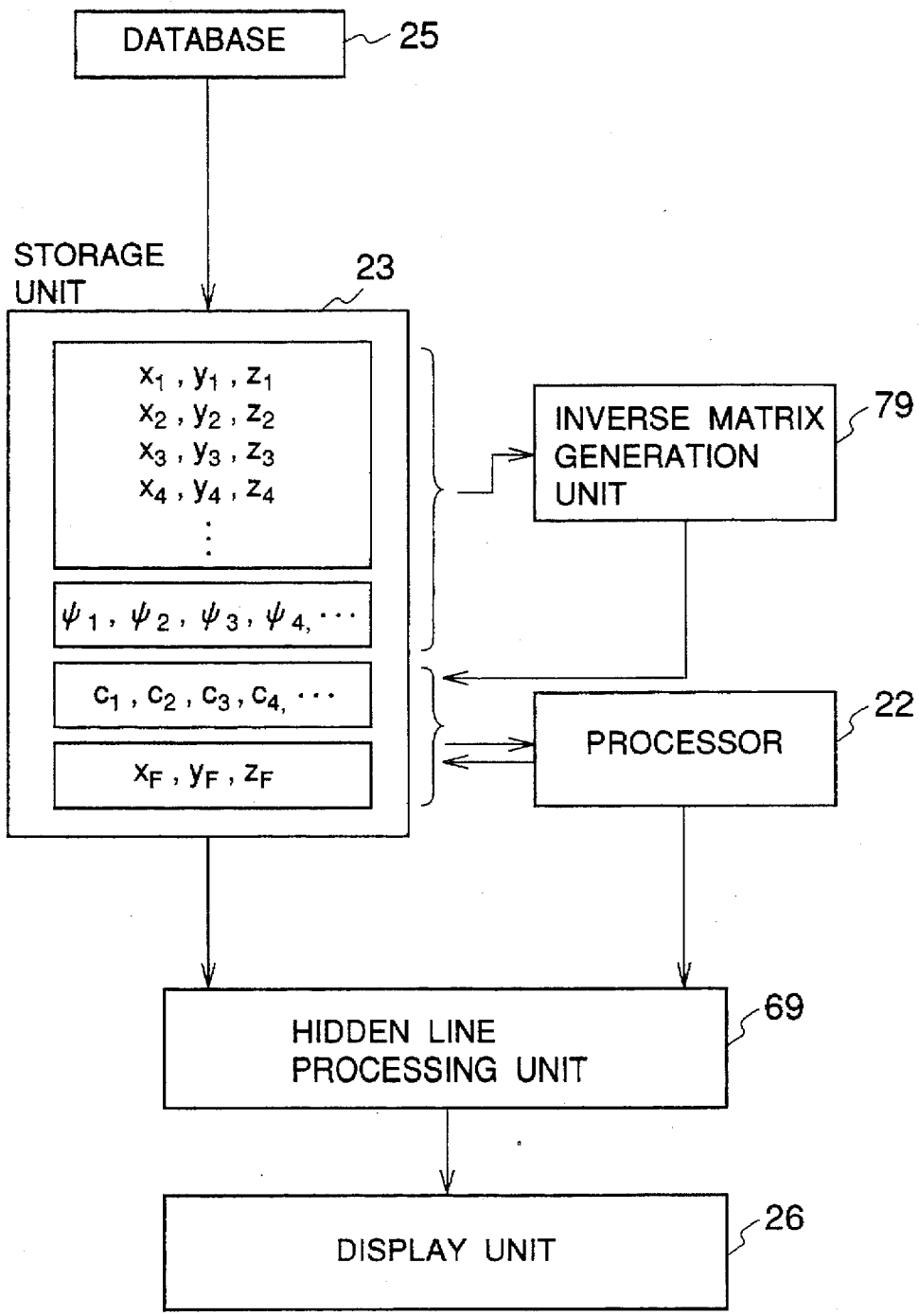
FIG. 13 is a system block diagram showing an essential part of the third embodiment.

FIG. 13 shows the construction of the third embodiment. A function processing system 71 shown in FIG. 13 includes a processor 22, a storage unit 23, a database 25, a display unit 26, a hidden line processing unit 69 and an inverse matrix generating unit 79 which are connected as shown. The illustration of the molecular orbital calculation means 24 is omitted in FIG. 13.

The processor 22 selects the lattice point coordinates $(x_1, y_1, z_1)$, $(x_2, y_2, z_2)$, $(x_3, y_3, z_3)$ and $(x_4, y_4, z_4)$ in the vicinity of the space coordinate $(x_F, y_F, z_F)$ which is to be obtained, from the information such as the molecular coordinate obtained from the database 25. In addition, the processor 22 stores the selected lattice point coordinates $(x_1, y_1, z_1)$, $(x_2, y_2, z_2)$, $(x_3, y_3, z_3)$ and $(x_4, y_4, z_4)$ together with the function values $\psi_1$, $\psi_2$, $\psi_3$, $\psi_4$, . . . into the storage unit 23. The number of lattice points in the vicinity of the space coordinate $(x_F, y_F, z_F)$ and the number of functions are determined by the number of coefficients in the interpolating function. For example, the number of lattice points in the vicinity of the space coordinate $(x_F, y_F, z_F)$ is 4 in the case of the first order equation, and is 10 in the case of the second order equation.

Based on the values stored in the storage unit 23, the inverse matrix generating unit 79 determines the coefficients $c_1$, $c_2$, $c_3$, $c_4$, . . . of the interpolating function. In addition, the processor 22 calculates the predicted value $\psi_F$ of the function value at the coordinate $(x_F, y_F, z_F)$.

Finally, the hidden line processing unit 69 carries out the hidden line processing, and the image which has been subjected to the hidden line processing is displayed on the display unit 26.

In each of the embodiments described heretofore, the multivariable function may be replaced by a linear combination of the products of at least two or mode single variable functions or, replaced by an approximation which is the product of the single variable functions. In addition, the single variable function may be an elementary function or a combination of elementary functions.

Moreover, the present invention is applied to the molecular design support system in the second and third embodiments described above, however, the second and third embodiments may be applied similarly to computer support systems or the like which process information related to fluids, thermal conduction and the like, where various multivariable functions are to be visualized.

Further, the present invention is not limited to these embodiments, but various variations and modifications may be made without departing from the scope of the present invention.

What is claimed is:

1. A function processing system for processing functions for a molecular system of materials utilizing a computer system to make a three-dimensional display on a screen of a display by connecting a plurality of lattice points of a space coordinate in a three-dimensional space region, said function processing system comprising:

computing means for computing a function value at each of the lattice points by a multivariable function having the space coordinate as an independent variable, said computing means replacing the multivariable function directly by a product of a predetermined number of single variable functions and computing each of the single variable functions in advance so that the multivariable function is computed based on function values of each of the single variable functions;

storage means, coupled to said computing means to form the computer system, for storing the function values of the single variable functions which are computed in advance by said computing means, said computing means reading the stored function values of the single variable functions from said storage means when computing the multivariable function; and output means for outputting the function values computed by said computing means to provide the three-dimensional display of lattice points.

2. The function processing system as claimed in claim 1, wherein said computing means computes the multivariable function which is replaced by a linear combination of products of at least two or more single variable functions.

3. The function processing system as claimed in claim 1, wherein said computing means computes the multivariable function which is replaced by an approximation which is a product of the single variable functions.

4. The function processing system as claimed in claim 1, wherein said storage means stores function values of the single variable functions and function values of elementary functions forming the single variable functions.

5. The function processing system as claimed in claim 4, wherein said computing means obtains round numbers of the elementary functions by interpolating the function values of the elementary functions stored in said storage means by obtaining a variable range from an internal expression of a floating point.

6. The function processing system as claimed in claim 4, wherein said computing means obtains round numbers of the single variable functions by interpolating the function values of the single variable functions stored in said storage means.

7. The function processing system as claimed in claim 5, wherein said computing means calculates round numbers of the single variable functions from the round numbers of the elementary functions.

8. The function processing system as claimed in claim 4, wherein said computing means calculates round numbers of the elementary functions with respect to predetermined variable values by a linear interpolation.

9. The function processing system as claimed in claim 4, wherein said computing means obtains round numbers of the elementary functions by forming a spline function from the elementary function and obtaining a spline function value with respect to a predetermined variable value.

10. The function processing system as claimed in claim 1, wherein said computing means calculates a differential function value related to each coordinate of the single variable function and stores the calculated differential function value in said storage means.

11. The function processing system as claimed in claim 1, wherein said multivariable functions are molecular information which is obtained by theoretical chemical calculations when making a molecular design.

12. The function processing system as claimed in claim 11, wherein said molecular information is obtained by computations based on molecular orbital calculations.

13. The function processing system as claimed in claim 11, wherein said molecular information includes at least electron state information.

14. The function processing system as claimed in claim 1, wherein said storage means stores values of the single variable functions, function values of the single variable functions which are related to each of coordinates X and X' and differential functions which are computed by said computing means for each lattice width of the coordinates X and X', where X denotes a coordinate system of the multivariable functions and X' denotes a coordinate system having an axis in a direction matching a line of sight with respect to the screen of the display when projecting an isoplethic surface which is defined by the multivariable functions on the screen of the display; and wherein said function processing system further comprises hidden line processing means for carrying out a hidden line processing including a visibility/invisibility judgement based on the values stored in said storage means.

15. The function processing system as claimed in claim 14, wherein the multivariable functions are scalar functions or vector functions.

16. The function processing system as claimed in claim 14, wherein said computing means includes:

unitary transformation means for transforming a linear combination coefficient into a new linear combination coefficient by making a linear transformation depending on the single variable functions, based on the coordinate system X and linear combination coefficients of the functions forming the single variable functions.

17. The function processing system as claimed in claim 14, wherein said computing means approximates a function value related to an arbitrary lattice point in the coordinate system X by a predicted value of a function value related to a different lattice point which is located along the same direction as the line of sight of said arbitrary lattice point, by obtaining the predicted value through interpolation of function values at a plurality of lattice points in a vicinity of said different lattice point.

18. The function processing system as claimed in claim 17, wherein said computing means includes:

inverse matrix generating means for determining coefficients of an interpolating function by use of an inverse matrix.

19. The function processing system as claimed in claim 17, wherein said computing means approximates the predicted value from a linear relationship equation, a first order equation or an equation of an order greater than or equal to two.

20. A function processing system for processing functions for a molecular system of materials utilizing a computer system to make a three-dimensional display on a screen of a display by connecting a plurality of lattice points of a space coordinate in a three-dimensional space region, said function processing system comprising:

computing means for computing a function value at each of the lattice points by a multivariable function having the space coordinate as an independent variable, said computing means having means for replacing directly the multivariable function by a product of a predetermined number of single variable functions and means for computing each of the single variable functions in advance so that the multivariable function is computed based on function values of each of the single variable functions;

storage means, coupled to said computing means, for storing the function values of the single variable functions which are computed in advance by said computing means, said computing means reading the stored function values of the single variable functions from said storage means when computing the multivariable function; and output means, coupled to said computing means, for making a three-dimensional image at the lattice points of the three-dimensional space based on the function values which are computed by said computing means.

21. A computer program product for controlling a computer to produce a three-dimensional display of a plurality of lattice points connected in a three-dimensional space region on a screen of a display, each lattice point having a space coordinate, said computer program product comprising:

at least one recording medium readable by the computer;

executable single variable instructions recorded on said at least one recoding medium to control calculation and storage of function values of single variable functions related to the lattice points;

executable read instructions recorded on said at least one recording medium to control reading of the function values of the single variable functions from said at least one recording medium;

executable multivariable instructions recorded on said at least one recording medium to control computation at each of the lattice points of a function value for a multivariable function, having the space coordinate as an independent variable, by directly replacing the multivariable function with a product of a predetermined number of the single variable functions using the function values previously stored on said at least one recording medium and read by said executable read instructions; and executable display instructions recorded on said at least one recording medium to generate the three-dimensional display of the lattice points based on the product of the predetermined number of the single variable functions calculated at each of the lattice points.

22. A computer program product as claimed in claim 21, wherein said executable single variable instructions stored on said at least one recording medium calculate the function values of the single variable functions as related to each of coordinates X and X' and differential function values computed for each lattice width of the coordinates X and X', where X denotes a coordinate system of the multivariable functions and X' denotes a coordinate system having an axis in a direction matching a line of sight with respect to the screen of the display when projecting an isoplethic surface defined by the multivariable functions on the screen of the display; and wherein said computer program product further comprises executable hidden line instructions recorded on said at least one recording medium to control hidden line processing by the computer, including visibility/invisibility judgement based on the function values and the differential function values stored on said at least one recording medium.

23. A method of producing a three-dimensional display of a plurality of lattice points connected in a three-dimensional space region on a screen of a display in a computer system, each lattice point having a space coordinate, said method comprising:

computing function values of single variable functions related to the lattice points and storing the function values in a storage device;

computing at each of the lattice points a function value for a multivariable function, having the space coordinate as an independent variable, by directly replacing the multivariable function with a product of a predetermined number of the single variable functions using the function values previously stored and read from the storage device; and producing a three-dimensional image in the three-dimensional space based on the product of the function values of the single variable functions at the lattice points.

\* \* \* \* \*

UNITED STATES PATENT AND TRADEMARK OFFICE
CERTIFICATE OF CORRECTION

PATENT NO. : 5,742,290
DATED : Apr. 21, 1998
INVENTOR(S) : HAYANO et al.

It is certified that error appears in the above-identified patent and that said Letters Patent is hereby corrected as shown below:

Col. 8, line 32, change "t=$\zeta_i Y_i$," to -- t= $\zeta_1 \tau_i$ ,

Col. 11, formulas (18), in the second formula, change " $\frac{dG_h}{dy}$ " to -- $\frac{dG_k}{dy}$ --.

Signed and Sealed this

Thirteenth Day of October 1998

Attest:

BRUCE LEHMAN

Attesting Officer

Commissioner of Patents and Trademarks